United States Patent [19]

Warriner

[11] Patent Number: Plant 6,693

[45] Date of Patent: Mar. 28, 1989

[54] ROSE PLANT JACBED

[75] Inventor: William A. Warriner, Tustin, Calif.

[73] Assignee: Jackson & Perkins Company, Medford, Oreg.

[21] Appl. No.: 65,013

[22] Filed: Jun. 19, 1987

[51] Int. Cl.[4] ..... A01H 5/00

[52] U.S. Cl. ..... Plt./10

[58] Field of Search ..... Plt. 10, 20, 21, 29

*Primary Examiner*—James R. Feyrer

*Attorney, Agent, or Firm*—Majestic, Gallagher, Parsons & Siebert

[57] ABSTRACT

A rose variety of the miniature class is provided having a very vigorous, upright bush form that is densely branched bearing abundant clusters of red flowers and having foliage with strong resistance to powdery mildew.

1 Drawing Sheet

SUMMARY OF THE INVENTION

The present invention relates to a new and distinct variety of rose plant of the miniature class, which was originated by me by crossing an unnamed variety with an unnamed variety.

The primary objective of this breeding was to produce a new rose variety of the miniature class exhibiting compact, dense plant habit, clean foliage and red flowers. This objective was substantially achieved, along with other desirable improvements, as evidenced by the following unique combination of characteristics which are outstanding in the new variety and which distinguish it from its parents as well as from all other varieties of which I am aware. For example, this new rose variety has:

1. A plant habit with strong basal dominance, producing numerous canes from the plant base;
2. Abundant foliage;
3. Strong resistance to rose powdery mildew;
4. Blooms in clusters and also on single stems;
5. Non-fading red colored blooms;
6. Little or no fragrance;
7. Blooms with rigidity.

Asexual reproduction of this new variety by cutting, as performed at Wasco, Calif., shows that the foregoing characteristics and distinctions come true to form and are established and transmitted through succeeding propagation.

DESCRIPTION OF THE DRAWING

The accompanying illustration shows typical specimens of the vegetative growth and flowers of this new variety in different stages of development, depicted in color as nearly true as it is reasonably possible to make the same in a color illustration of this character.

DETAILED DESCRIPTION OF THE INVENTION

The following is a detailed description of my new rose cultivar, which has been denominated "Jacbed". Color terminology is in accordance with The Royal Horticultural Society Colour Chart except where an ordinary dictionary significance for the color is apparent.

Observations of the buds and flowers were made from specimens grown in a garden at Irvine, Calif. in May.

Flower

The bud size is one-half inch when the petals start to unfurl. The bud form is short, pointed ovoid. The bud color when sepals first divide is near Red 44A; when half blown, the upper side of petals is near Red 44A and the lower side of petals is near Red 44A. The sepals have a color near Green 137B. The sepals' surface texture is mostly smooth but occasional stipitate. There are three appendaged sepals normally appendaged, and two unappendaged sepals with hairy edge. The receptacle color is near Green 137B with a funnel shape, broad size and smooth, glossy surface. The peduncle is of medium length, and smooth, slightly glandular surface. Peduncle color is medium green and the peduncle is stiff and erect. The petals fold out slowly.

Bloom

Bloom size is small, with an average open size of two inches, borne in clusters. The clusters are rounded. The stems are strong and short. The form when first open is high center. This form is retained to the end. Under normal conditions there are thirty to thirty-five petals. The upper side of petals is Red 44B, as is the reverse side of the petals. The base of petals is near white with the major color being near Red 44A to 44B. There are no variegations except for an occasional white midrib. The general tonality at the end of the first day is near Red 44A. At the end of the third day, the color is still near Red 44A.

There is very little fragrance. The petal texture is thick, very strong, and stiff, of a broadly oval shape with the tips being slightly recurved.

The arrangement is imbricated with few petaloids in the center. The blooms drop off cleanly, last on the plant for a long period, and last as a cut flower for a long time.

Reproductive Parts

The anthers are medium, of yellow color and arranged regularly around the styles. The filaments are yellow, the pollen is gold yellow, the styles are reddish, and the stigmas are white.

Plant

A very vigorous, upright bush form that is densely branched.

Foliage

Small size, abundant in quantity. The new foliage is near Greyed-Purple 187B, and the old foliage is near Green 137A. Normal mid-stem leaves have five to seven leaflets.

The leaflets are of a pointed, elliptic shape, are leathery, and have a serrated edge. The serration is single and small in size. Petiole rachis is green or reddish and petiole underside has prickles. Stipules are long and bearded. The foliage is resistant to mildew under normal growing conditions at Irvine, Calif.

Wood

New wood is light green, with a smooth bark. Old wood is green with a smooth bark.

Prickles

There are many prickles on main canes from the base and on laterals from the main canes. The form is long and hooked slightly downward. Color when young is red.

Small Prickles

There are no small prickles on the main stalks or on the laterals.

Additional Distinguishing Traits

The plant reaches a height in California of approximately three to four feet and a width of about two feet to three feet.

Parentage

Both the seed parent and the pollen parent were unnamed varieties.

Classification

Botanical is rosa hybrid. Commercial is miniature.

I claim:

1. A new and distinct variety of rose plant and parts thereof of the miniature class substantially as herein shown and described, characterized particularly as to novelty by the compact, dense plant form having abundant, mildew-resistant foliage and bearing red flowers in clusters and also on single stems.

* * * * *

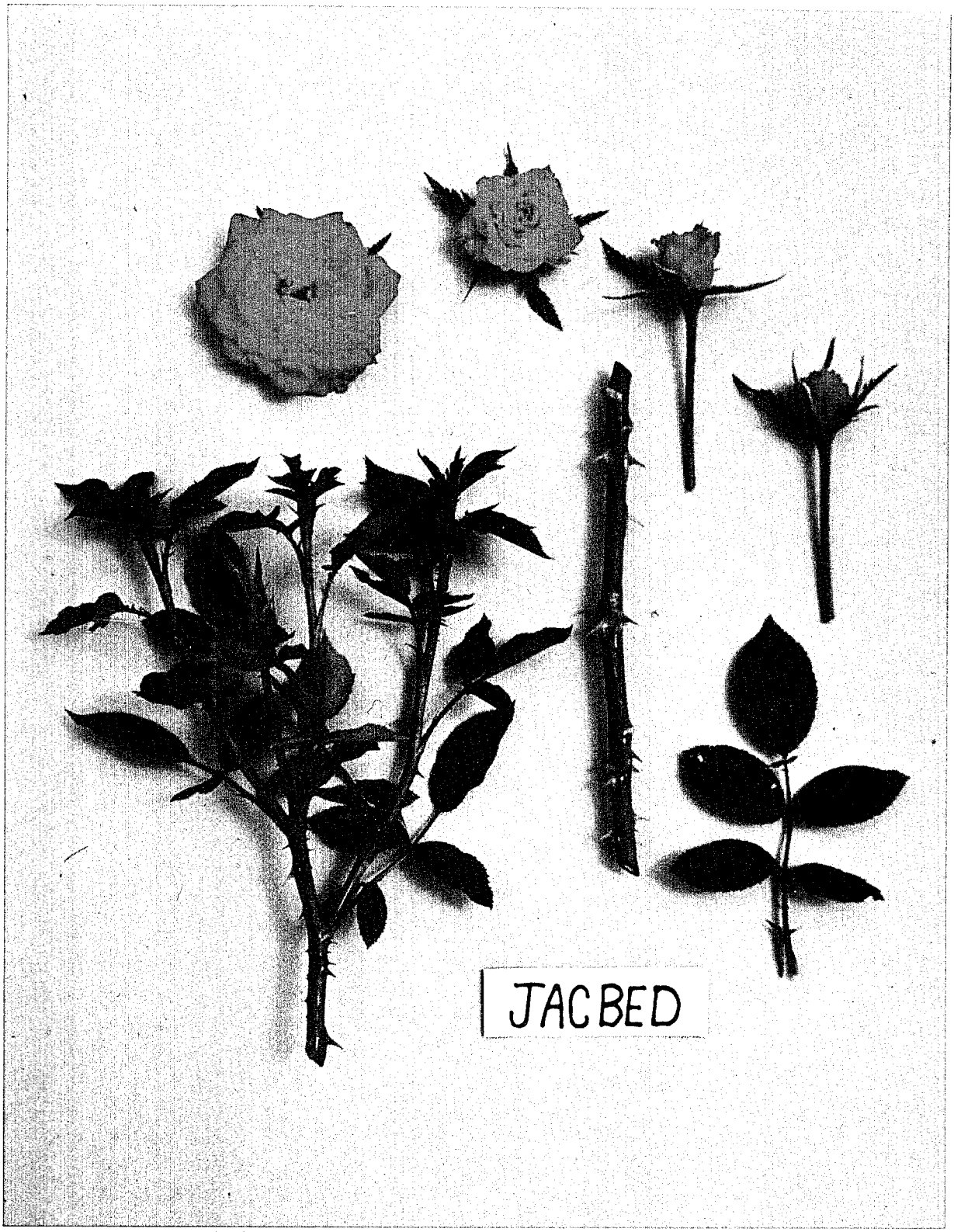
JACBED